United States Patent [19]

Howarth

[11] 4,012,197

[45] Mar. 15, 1977

[54] TITRATION APPARATUS AND METHOD THEREFOR

[75] Inventor: John J. Howarth, Monte Sereno, Calif.

[73] Assignee: Measurex Corporation, Cupertino, Calif.

[22] Filed: Nov. 7, 1975

[21] Appl. No.: 629,859

[52] U.S. Cl. .................... 23/230 A; 23/253 A; 162/49
[51] Int. Cl.² ................ G01N 31/16; D21C 3/24
[58] Field of Search ......... 23/230 R, 230 A, 253 A, 23/253 R; 204/1 T, 195 T; 162/49

[56] References Cited

UNITED STATES PATENTS

| | | | |
|---|---|---|---|
| 2,977,199 | 3/1961 | Quittner | 23/230 R |
| 2,989,377 | 6/1961 | Leisey | 23/230 R |
| 3,290,116 | 12/1966 | Carroll | 23/230 R |
| 3,308,041 | 3/1967 | Strickler | 204/1 T |
| 3,625,655 | 12/1971 | Culp et al. | 23/253 R |
| 3,888,726 | 6/1975 | Hultman | 162/49 |
| 3,904,370 | 9/1975 | Robison | 23/230 A |

Primary Examiner—R.E. Serwin
Attorney, Agent, or Firm—Flehr, Hohbach, Test, Albritton & Herbert

[57] ABSTRACT

A titration apparatus and method therefor for determining the available alkali in a Kamyr or batch digester includes a sample vessel and a reference vessel suspended within the system itself in either the digester or associated pipelines. Carbon dioxide is used as a titrant and the end point is determined by a computer monitoring conductivity.

14 Claims, 10 Drawing Figures

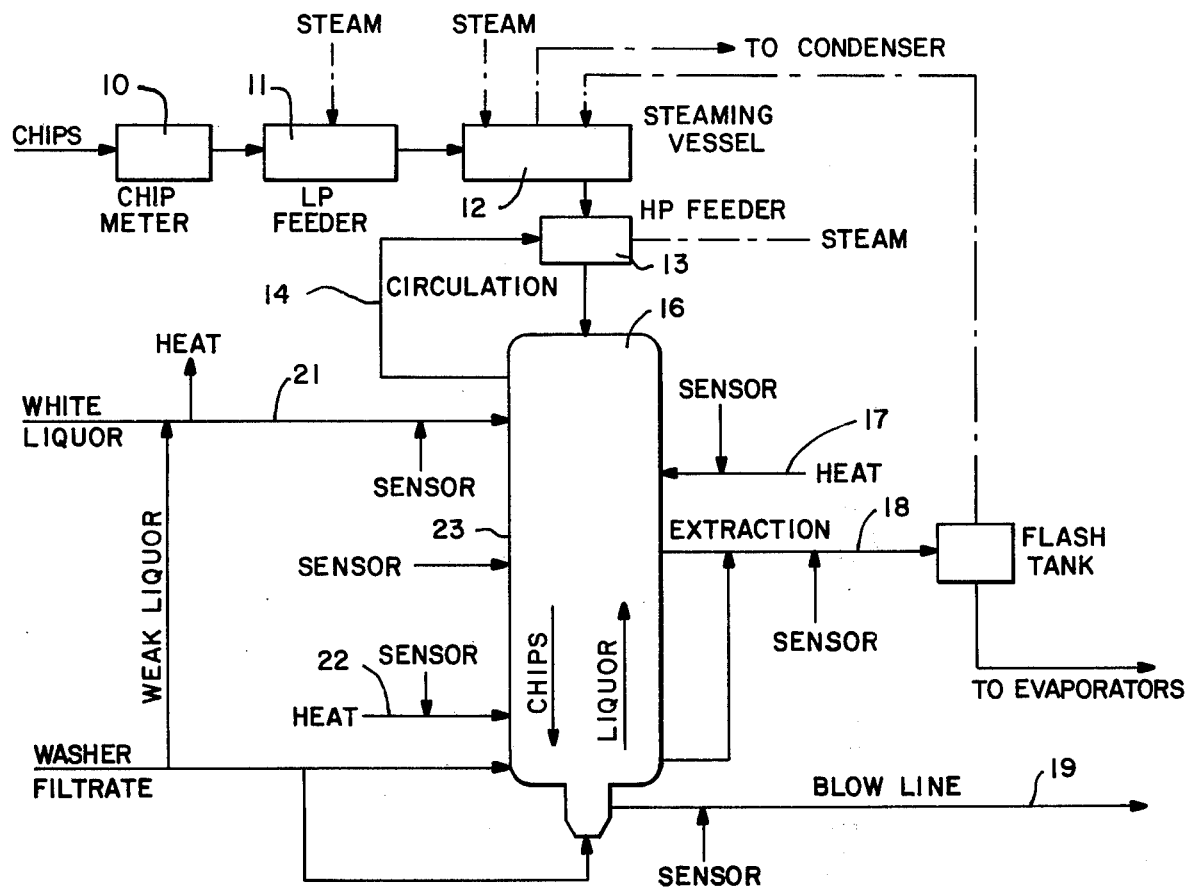
FIG.—1
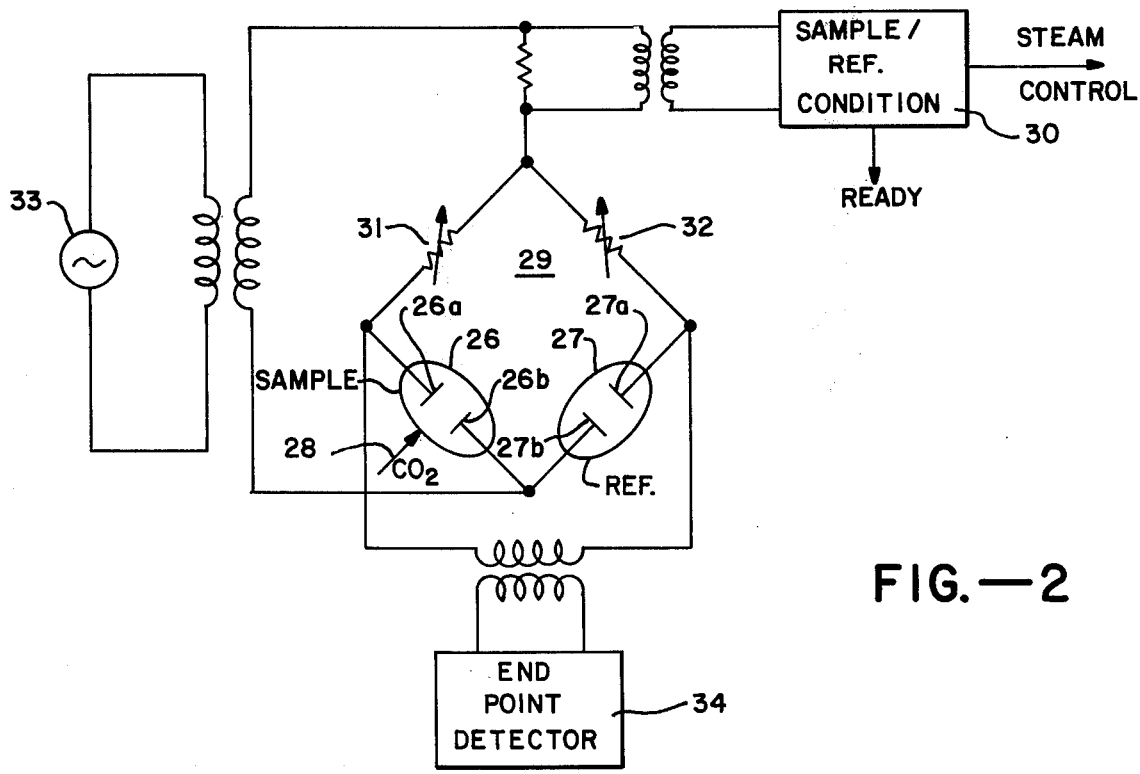
FIG.—2

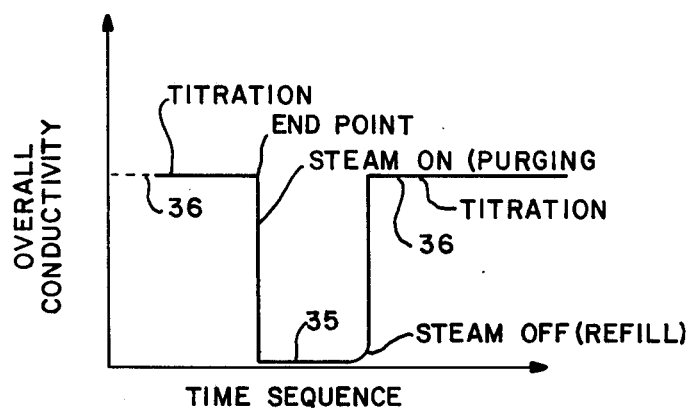
FIG.—3
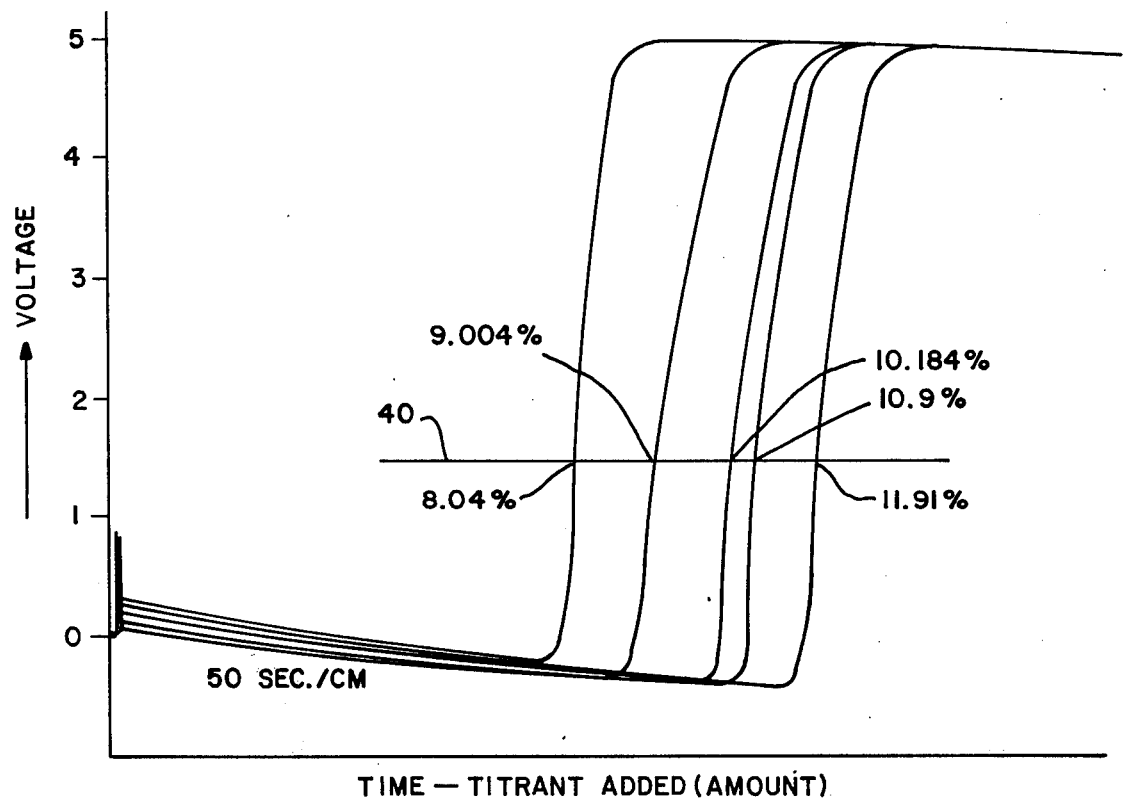
FIG.—4
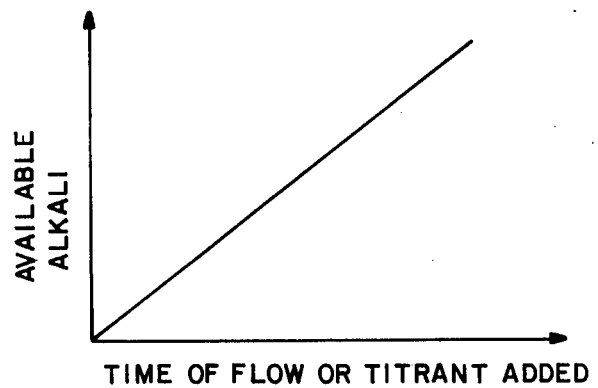
FIG.—5

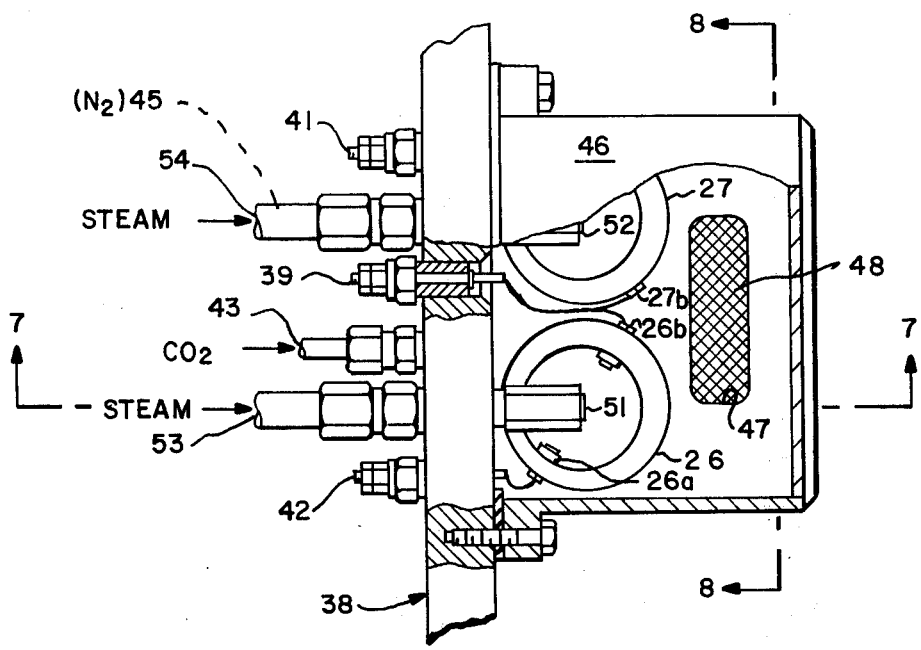
FIG.—6
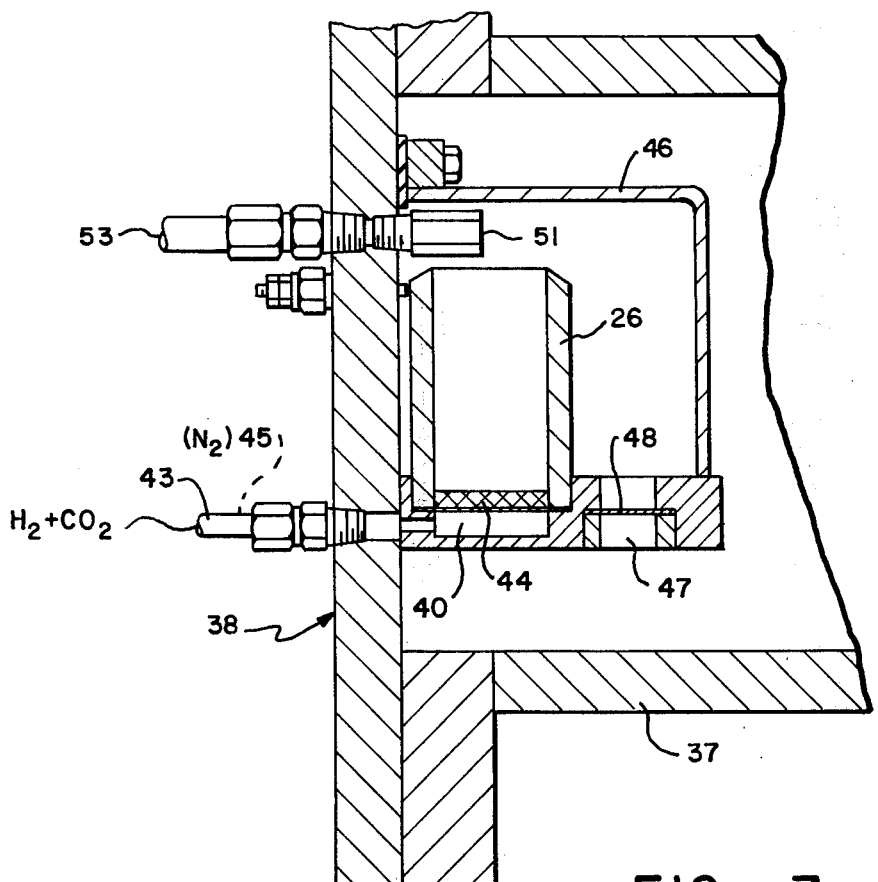
FIG.—7

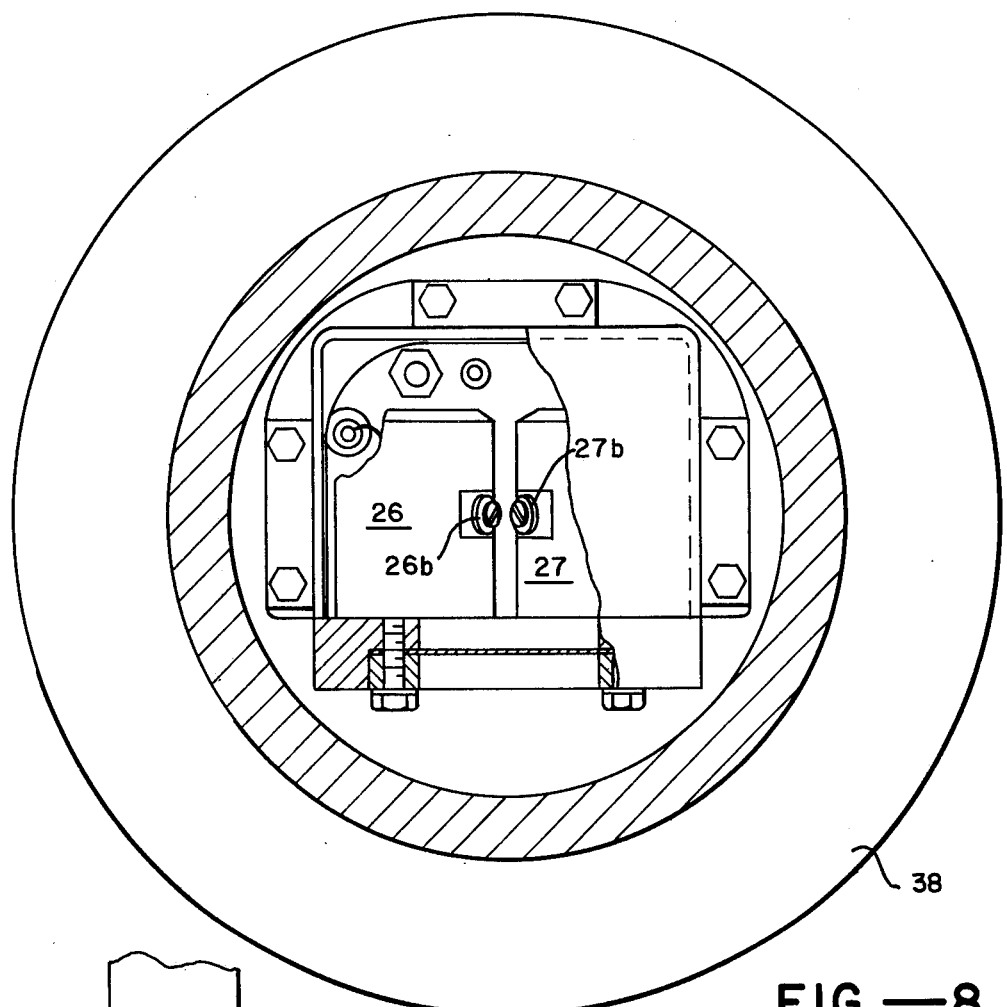
FIG.—8
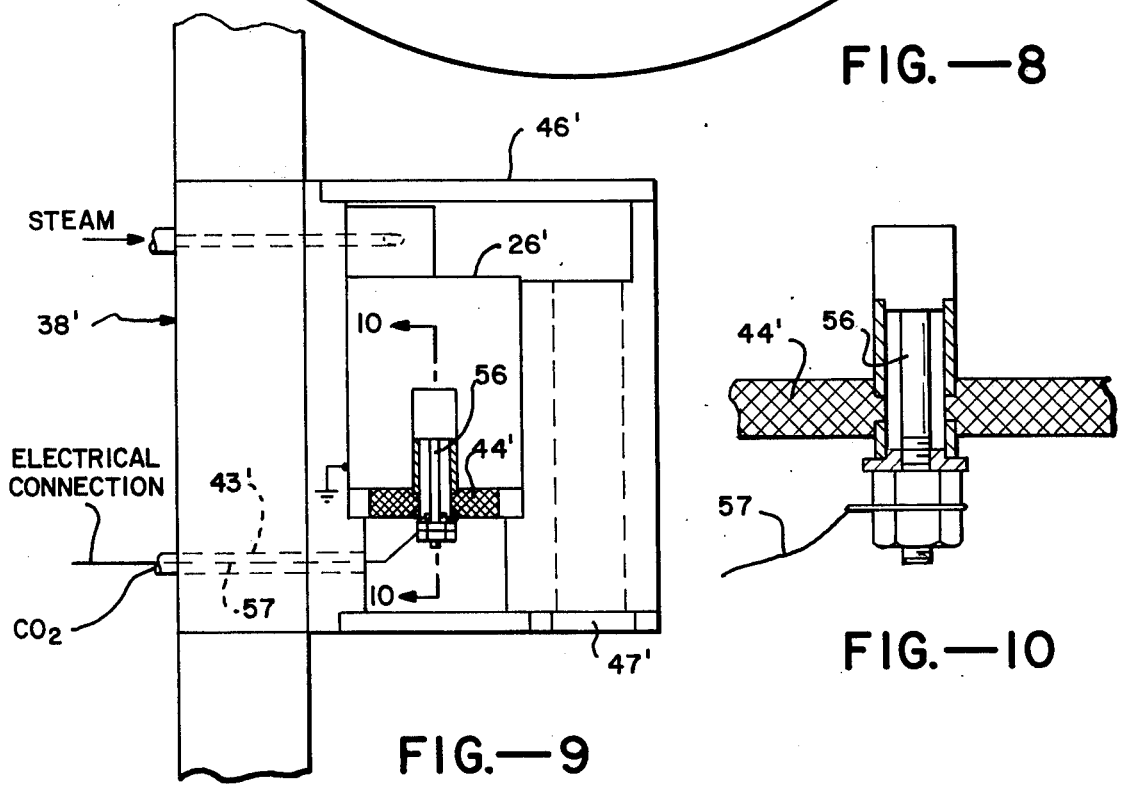
FIG.—9
FIG.—10

TITRATION APPARATUS AND METHOD THEREFOR

BACKGROUND OF THE INVENTION

The present invention is directed to a titration apparatus and method therefor and more specifically to the on-line measurement of the available alkali in a Kamyr or batch digester being used for processing paper pulp.

As stated in a paper entitled "Computer Control in Pulp and Paper 1961–1969" by Donald B. Brewster and Andrew K. Bjerring in the *Proceedings of the IEEE*, Volume 58, No. 1, Jan. 1970, page 51, "at the present time there is no effective commercial on-line instrument available for measuring K number" (in a Kamyr digester). "Manual tests on samples taken from the blow line or washer (of the digester) are performed, usually once per hour." The purpose of the pulp digester is, of course, to convert the wood into fiber. This is achieved in the digester by treating the wood chips with a white liquor which consists of a solution of sodium sulfide and sodium hydroxide. Both high heat and pressure are present in the digester to provide delignification. Lignin accounts for about 30% of the wood and it is removed to allow easy separation and bleaching of the cellulose fibers. The usual measure of the extent of delignification is the "K number"; the lower the K number the lower the residual lignin. An alternate to the measure of K number is the measure of the alkalinity of the liquor in the digester indicating the extent of the reaction between the alkali and the lignin.

With an on-line measurement of K number or alkalinity much better control of the digester is possible. At the present time as discussed on page 55 of the Brewster article the most feasible method of K number regulation is to use feedforward control and keep the following five factors constant: alkali to wood ratio, liquor to wood ratio, temperature, residence time and chip level control. In order to stabilize this feedforward control the one hour sample of the blow line is utilized as a feedback control. It is apparent that because of the long time delay involved to obtain a K number sample the entire control scheme is unsatisfactory. To remedy the foregoing a Swedish company under the name ASEA utilizes an on-site titrator to determine alkalinity with a "mechanical man" to obtain the sample. This is not an effective on-line measurement since the time required is over ten minutes. Also the moving parts of the mechanical man, especially under the high pressure and temperature conditions in a typical digester, make the design, operation, and maintenance of such a system impractical.

OBJECTS AND SUMMARY OF THE INVENTION

It is, therefore, an object of the present invention to provide improved on-line titration apparatus and method therefor which is suitable for use in severe ambient environments.

In accordance with the above object there is provided a titration apparatus for the on-line measurement of the concentration of an analyte in a container. A sample vessel is suspended inside the container from a wall. Means are provided for sensing the conductivity of the analyte in the vessel. Pipe means convey a measured amount of titrant to one of the vessels. Electrical means sense an end point condition between the analyte and titrate. Means are provided for purging the vessel of analyte and titrant.

A method is also provided for the on-line measurement of the concentration of an analyte in a container having a sample vessel suspended inside the container from a wall. The analyte is trapped in the sample vessel and thereafter a titrant is injected into the sample vessel. The sample vessel is isolated during the titrant injection. An abrupt change in the conductivity of the analyte in the sample vessel is sensed during the injection of the titrant. Thereafter, the sample vessel is purged.

BRIEF DESCRIPTION OF THE DRAWINGS

FIG. 1 is a block diagram of a digester;

FIG. 2 is a simplified electrical schematic embodying the present invention;

FIG. 3 is a time sequence diagram useful in understanding the operation of the invention;

FIG. 4 is a graph useful in understanding the operation of the invention;

FIG. 5 is a graph illustrating the operation of the invention;

FIG. 6 is a top view partially cut away illustrating a portion of FIG. 2;

FIG. 7 is a cross sectional view substantially taken along line 7—7 of FIG. 6 and including additional peripheral structure;

FIG. 8 is a cross sectional view taken substantially along the line 8—8 of FIG. 6 showing the additional peripheral structure of FIG. 7;

FIG. 9 is a cross sectional view of an alternative embodiment of FIG. 7; and

FIG. 10 is an enlarged cross sectional view taken along line 10—10 of FIG. 9.

DETAILED DESCRIPTION OF THE PREFERRED EMBODIMENTS

FIG. 1 illustrates a Kamyr digester in schematic form. The digester is well-known in the art except for the technique of sensing the alkali concentration at the various levels. In general in operation chips are metered volumetrically by a chip meter 10 and a low pressure feeder 11 into a steaming vessel 12 whose prime function is to drive off air, the presence of which would inhibit liquor penetration. The chips are then mixed with circulating liquor from the circulating line 14 in high pressure feeder 13 and forced into the top separator section of the main digester container 16. In the top separator excess liquor is separated, mixed with the white liquor makeup, and recirculated. The chips settle onto the top of the chip-liquor mass already in the impregnation zone of the digester. As discussed above, white liquor consists of a solution of sodium sulfide and sodium hydroxide.

After about forty minutes residence in the digester heat is added at point 17 by circulating a portion of the liquor through heating coils. This raises the temperature so that delignification occurs. The cooking zone extends down to the extraction point 18 which extracts the spent liquor (now known as black liquor) for recovery in a manner well-known in the art. Pulp is removed from the bottom of the digester about four hours after it leaves the cooking zone. Such removal is accomplished via the blow line 19. White liquor is also added at the line 21 along with heat. Finally heat is added via the recirculating line 22.

In accordance with the invention the sensor may be located at several locations in the digester to detect the available alkali. This includes the white liquor input line 21, a side wall portion 23 of the digester, the heat input 22, the heat input 17, extraction output 18 and the blow line 19. Depending on the preferred control scheme one or more of the sensors may be utilized for appropriate feedback control. Thus, direct control of K number may be effected.

A typical sensor is illustrated in schematic form in FIG. 2 and includes a sample vessel 26 and a reference vessel 27 which are both suspended with a vertical orientation inside a contained volume associated with the digester. It may either be in the side wall 23 or in one of the many recirculating pipe lines shown. Vessels 26 and 27 also include the associated electrodes 27a, b and 26a, b. These electrodes as will be apparent from the discussion below measure the change in conductivity of the liquid being measured when a titrant is added to the liquid which is more scientifically termed an analyte. Titration is accomplished by the addition of carbon dioxide by a line 28 to the sample vessel 26. The electrodes and their associated vessels are part of an overall Wheatstone bridge 29 which includes the adjustable balancing resistors 31 and 32. A generator 33 drives the bridge. An end point detector 34 is connected to the bridge to provide a signal indicative of the available alkali in the sample vessel. In practice detector 34 would include an amplifier connected to a minicomputer.

The use of a separate reference vessel (which, of course has no titrant added to it) insures that chemical changes which occur in the process during measurement are compensated for and also provides a bridge type measurement which is inherently highly accurate. However in many applications this may not be necessary and the reference vessel may be replaced by a simple reference resistor.

Referring now also to FIG. 3 the overall conductivity of bridge 29 is sensed by a sample/reference condition unit 30. When neither vessel 26 or 27 contains any liquid a low conductivity condition (level 35) occurs indicating that the vessels have been purged. However, after refilling a normal conductivity level 36 is present. These levels, as will be discussed below, are useful for sequencing purposes.

FIG. 4 illustrates typical test results with different percentages of alkalinity in a constant volume. The horizontal axis is time or amount of titrant added (since the carbon dioxide flow is constant) versus the output voltage to end point detector 34 of FIG. 2. The horizontal line 40 is a voltage level which establishes the end point at which the titrant balances the analyte and where an abrupt change in conductivity takes place. This change takes place when all of the available sodium hydroxide has reacted with the injected carbon dioxide to form sodium carbonate. The percentages of alkalinity are illustrated on the drawing of FIG. 4. Line 40 would normally be obtained either by an empirical selection of a voltage level and a particular environment or determining the midpoint between the maximum and minimum of the curves. FIG. 5 illustrates the substantially direct relationship between the amount of titrant added and the percentage of alkalinity or available alkali. Assuming a constant flow of titrant or carbon dioxide the time interval from the start of injection of the titrant to end point is therefore a measure of the concentration of the analyte. Thus the only electrical measurement necessary is the abrupt change in conductivity which is inherently highly immune to error; for example, inert material in the sample, electrode fouling, or drifts in associated electronics.

FIGS. 6, 7 and 8 illustrate the mechanical installation of the vessels 26 and 27 in the side wall of a container; either the wall of a pipeline to the digester or to the wall of the digester. Referring to FIGS. 7 and 8, the embodiment there illustrates a flange 37 which may extend from the side wall of the main portion of the digester or from one of the circulating heat pipes to which an assembly 38 carrying the measuring vessels may be bolted. As best shown in FIG. 6 vessel 26 includes the electrodes 26a and 26b; vessel 27 illustrates the electrode 27b. Electrodes 26b and 27b are connected together and brought out at terminal 39. Electrode 27a is brought out at terminal 41 and electrode 26a is brought out at terminal 42.

FIG. 7 shows the sample vessel 26 in its vertically upright position and a carbon dioxide titrant input pipe 43 which extends through the flange assembly 38 to the bottom of vessel 26. Carbon dioxide gas is introduced into the vessel through a fine or sintered metal disc illustrated at 44. This provides a finely diffused titrant into the liquid trapped in the vessel.

A second pipe 45 is connected to reference vessel 27 for injecting a neutral gas such as nitrogen into the bottom of the vessel 27 in the same manner as carbon dioxide is injected into sample vessel 26. This serves two purposes. First by balancing the flow of $N_2$ with $CO_2$ equal bubbling takes place through the analyte in each vessel. Thus any change in conductivity due to bubbling is balanced out. However, the main function of the $N_2$, which is chemically neutral is to provide for isolation of the contents of the sample and reference vessels during the titration by displacing the excess fluid from the covering 46.

More specifically such isolation is provided by covering means 46 which encloses the vessels 26 and 27 completely except for the constricted opening 47 which includes a wire mesh 48 to exclude solid particles. Covering 46 in combination with opening 47 in effect acts as a diving bell. The introduction of nitrogen during the titration tends to exclude further analyte from mixing with the analyte contained at least in sample vessel 26 by displacing it from the chamber. Moreover, covering 46 also allows more effective purging of the contents of the vessel by means of steam jetted from the nozzles 51 and 52 which are installed over and directed into the top openings of the vessels 26 and 27. The nozzles are coupled through the flange assembly 38 to pipes 53 and 54 respectively which in turn are connected to a source of pulsed steam. The steam is at a pressure of from 165–200 pounds per square inch which is sufficient to overcome the internal pressure of the container and still provide a strong jet. Steam is an ideal fluid for purging since after it is introduced it condenses and effectively collapses to allow vessels 26 and 27 to be recharged for a subsequent test. Alternatively, purging could be accomplished by a mechanical piston arrangement.

An alternative electrode arrangement is illustrated in FIGS. 9 and 10. A center electrode 56 is mounted on sintered disc 44'. The wall of vessel 26' is grounded to thus serve as the second electrode. The lead 57 is brought out through the carbon dioxide gas line. A similar modification is made to reference vessel 27.

In operation the vessels 26 and 27 and the associated volume enclosed by cover 46 is first purged of all liquid by use of the steam jets. The resulting low conductivity level 35 (FIG. 3) indicates a READY condition. See unit 30, FIG. 2. Cessation of the steam flow, controlled by unit 30, allows the steam in the chamber to cool and condense (or collapse) allowing liquid analyte to enter the vessels through opening 47 where it is essentially trapped. After the vessels are filled the carbon dioxide titrant is carefully metered into sample vessel 26 at a constant rate. Concurrently nitrogen is bubbled through reference vessel 27 as for reasons discussed above. Thereafter the end point is detected and utilized by an associated computer or even manual means to directly determine the alkalinity.

If desired and to avoid pressure pulses, the carbon dioxide may be continuously injected. Here the start of injection time may be taken as the steam off point (FIG. 3) since the condensation of the steam and subsequent refilling is almost instantaneous as illustrated. Also the measurement of total conductivity (its change in level) may be used to initiate the timing.

The titrant used is carbon dioxide since the reaction of the carbon dioxide with the solution of white liquor, which as discussed above consists of sodium hydroxide and sodium sulfide, produces sodium carbonate which is already present in the digester. Also, it does not add to the volume of the trapped sample and is very easy to manipulate. An alternative titrant is hydrochloric acid but this would be less satisfactory in the preferred embodiment in that sodium chloride would be produced from the titration which is not naturally occurring in the process and would present corrosion problems. Also in some types of digesters such as the acid sulfite process the titrant would be preferably ammonia.

In summary, an improved titration apparatus has been provided for the on-line measurement of the concentration of an analyte under severe ambient conditions. No sample need be taken such as by a mechanical man out of the digester reactor or the associated pipelines and no moving parts are involved. Also no sample conditioning such as cooling and filtering is required. This is especially beneficial under the severe ambient conditions which in addition to pressure and temperature includes a corrosive atmosphere. The use of both a sample and a reference cell in conjunction with the Wheatstone bridge arrangement provides a very sensitive measurement of end point which is immune to changes in other parameters of the process as discussed above.

What is claimed is:

1. Titration apparatus for the on-line measurement of the concentration of an analyte in a container within a reaction system comprising: a sample vessel suspended inside said container from a wall; means for sensing the conductivity of analyte in said vessel; pipe means for conveying a measured amount of titrant to said vessel; electrical means for sensing an end point condition between said analyte and titrant; means for isolating said analyte which has been trapped in said vessel from the other analyte in said reaction system during introduction of said titrant into said vessel and means for purging said vessel of said analyte and titrant.

2. Apparatus as in claim 1 where said purging means includes a source of gas.

3. Apparatus as in claim 2 where said gas is high pressure steam.

4. Apparatus as in claim 1 where said titrant is carbon dioxide.

5. Apparatus as in claim 1 where said isolating means includes a covering for said vessel with a constricted opening for transfer of said analyte between said container and said vessel and a source of neutral gas connected to inject said neutral gas into said covering to displace excess fluid from within said covering whereby said analyte is isolated.

6. Apparatus as in claim 5 together with a reference vessel suspended inside said container from a wall and within said covering and where said source of neutral gas is connected to said reference vessel and said pipe means for conveying said titrant is connected to said sample vessel.

7. Apparatus as in claim 1 where said end point condition is an abrupt change in said conductivity.

8. Apparatus as in claim 1 together with a reference vessel suspended inside said container from a wall and means for sensing the conductivity of analyte in said reference vessel, said electrical means for sensing said end point condition including means for comparing a difference between said sensed conductivities of said reference and sample vessels.

9. Apparatus as in claim 8 where said electrical means includes a Wheatstone bridge, with said sensing means forming two legs of the bridge.

10. Apparatus as in claim 9 where said bridge senses said end point condition which is an abrupt change in conductivity.

11. Apparatus as in claim 8 where said vessels have open tops and are vertically oriented.

12. Apparatus as in claim 9 together with means for sensing the overall conductivity of said bridge.

13. A method for the on-line measurement of the concentration of an analyte in a container within a reaction system having severe ambient conditions and having a sample vessel suspended inside said container from a wall comprising the following steps: trapping said analyte in said sample vessel; thereafter injecting a titrant into said sample vessel; isolating from said sample vessel from the other analyte in said reaction system during said titrant injection; and sensing an abrupt change in conductivity of said analyte in said sample vessel during injection of said titrant; and purging said sample vessel.

14. A method as in claim 13 where said titrant is injected at a constant rate and including the step of measuring the time interval from the start of said injection to said sensing of said abrupt change, the concentration of said analyte being proportional to said time interval.

* * * * *